US012589149B2

(12) United States Patent
Hsu et al.

(10) Patent No.: US 12,589,149 B2
(45) Date of Patent: Mar. 31, 2026

(54) METHOD OF MODULATING MUCOSAL IMMUNOGENICITY

(71) Applicant: ADVAGENE BIOPHARMA CO., LTD., Taipei City (TW)

(72) Inventors: Yu-Shen Hsu, Taipei City (TW); Mingi Chang, Taipei City (TW); Ssu-Wei Kang, Taipei City (TW)

(73) Assignee: ADVAGENE BIOPHARMA CO., LTD., Taipei City (TW)

( * ) Notice: Subject to any disclaimer, the term of this patent is extended or adjusted under 35 U.S.C. 154(b) by 1070 days.

(21) Appl. No.: 17/440,546

(22) PCT Filed: Mar. 18, 2020

(86) PCT No.: PCT/CN2020/079954
§ 371 (c)(1),
(2) Date: Sep. 17, 2021

(87) PCT Pub. No.: WO2020/187255
PCT Pub. Date: Sep. 24, 2020

(65) Prior Publication Data
US 2022/0143177 A1     May 12, 2022

Related U.S. Application Data

(60) Provisional application No. 62/820,966, filed on Mar. 20, 2019.

(51) Int. Cl.
*A61K 39/39* (2006.01)
*A61K 9/00* (2006.01)
(Continued)

(52) U.S. Cl.
CPC ............ *A61K 39/39* (2013.01); *A61K 9/0043* (2013.01); *A61K 9/006* (2013.01); *A61K 39/145* (2013.01);
(Continued)

(58) Field of Classification Search
CPC ........ A61K 2039/541; A61K 2039/545; A61K 2039/55544; A61K 2039/55555;
(Continued)

(56) References Cited

U.S. PATENT DOCUMENTS 5,562,910 A     10/1996  Daynes et al.
5,837,269 A     11/1998  Daynes et al.
(Continued)

FOREIGN PATENT DOCUMENTS

TW        200819536 A     5/2008
WO         9417823 A1     8/1994
(Continued)

OTHER PUBLICATIONS

FDA, U.S. Food & Drug Administration, published on Feb. 26, 2018.*
(Continued)

*Primary Examiner* — Bao Q Li
(74) *Attorney, Agent, or Firm* — HSML P.C.

(57) ABSTRACT

The present disclosure provides a novel method for modulating mucosal immune response, comprising administering an antigen to a mucosal site of a subject in need thereof, and administering an immunomodulator to a different anatomical mucosal site of said subject. The antigen may be administered to sublingual mucosa and the immunomodulator may be administered to intranasal mucosa. An immune response involving production of IgG and IgA against the antigen may be elicited.

18 Claims, 16 Drawing Sheets

| Flu B (μg) | 20 | 20 | 10 | 5 |
| LTh (αK) (μg) | - | 5 | 5 | 5 |
| Frequencies (weekly) | 3 | 3 | 3 | 3 |

Serum Anti-HA IgG
C57BL/6

| Flu B (μg) | 20 | 20 | 10 | 5 |
| LTh (αK) (μg) | - | 5 | 5 | 5 |
| Frequencies (weekly) | 3 | 3 | 3 | 3 |

Serum Anti-HA IgA
Balb/c

(51) Int. Cl.

| | |
|---|---|
| *A61K 39/145* | (2006.01) |
| *A61K 39/35* | (2006.01) |
| *A61K 39/36* | (2006.01) |
| *A61P 31/16* | (2006.01) |
| *A61P 37/04* | (2006.01) |
| *A61P 37/08* | (2006.01) |
| *A61K 39/00* | (2006.01) |

(52) U.S. Cl.
CPC .............. *A61K 39/35* (2013.01); *A61K 39/36* (2013.01); *A61P 31/16* (2018.01); *A61P 37/04* (2018.01); *A61P 37/08* (2018.01); *A61K 2039/545* (2013.01); *A61K 2039/55544* (2013.01); *A61K 2039/55555* (2013.01)

(58) Field of Classification Search
CPC ...... A61K 39/12; A61K 39/145; A61K 39/35; A61K 39/36; A61K 39/39; A61K 9/006; A61K 39/21; A61K 2039/575; A61K 2039/70; A61P 31/16; A61P 37/04; A61P 37/00; A61P 31/18; C12N 2760/16134; C12N 2740/16171; C12N 2740/16134; C07K 14/005
See application file for complete search history.

(56) References Cited

U.S. PATENT DOCUMENTS

| | | | | |
|---|---|---|---|---|
| 9,381,241 | B2 * | 7/2016 | Asai ..................... | A61K 38/162 |
| 2008/0102078 | A1 * | 5/2008 | Hsu ........................ | A61K 39/39 |
| | | | | 536/23.7 |
| 2008/0220519 | A1 | 9/2008 | Hsu et al. | |
| 2016/0151480 | A1 | 6/2016 | Zeng et al. | |
| 2016/0184424 | A1 | 6/2016 | Arwidsson et al. | |

FOREIGN PATENT DOCUMENTS

| | | | | |
|---|---|---|---|---|
| WO | WO2006126981 | A2 * | 11/2006 | ......... A61K 31/4745 |
| WO | 2016138504 | A1 | 9/2016 | |

OTHER PUBLICATIONS

Lycke et al. Nature Reviews Immunology vol. 12, pp. 592-605 , 2012.*

Patel et al. Critical Reviews in Therapeutic Drug Carrier Systems, 2014, vol. 31 (4), pp. 373-303.*

Rhee et al. Clin Exp Vaccine Res, Jul. 31, 2012 1 (1), 50-63.*

Komase et al. Vaccine, 1998, vol. 16, No. / 2/3, pp. 248-254.*

Office Action issued in corresponding European Application No. 20773152.2, dated Aug. 9, 2023, 10 pages.

Amarante-Mendes Gustavo P. et al: "Pattern Recognition Receptors and the Host Cell Death Molecular Machinery," Frontiers in Immunology, vol. 9, Oct. 16, 2018 (Oct. 16, 2018), XP093070352.

The extended European search issued in European Application No. 20773152.2, dated Aug. 3, 2022.

Munoz-Wolf Natalia et al: "Sublingual Immunotherapy as an Alternative to Induce Protection Against Acute Respiratory Infections", Journal of Visualized Experiments, No. 90, Aug. 30, 2014, 10 pages provided.

Tregoning J S et al: "A "prime-pull" vaccine strategy has a modest effect on local and systemic antibody responses to HIV gp140 in mice", PLOS ONE, Public Library of Science, US, vol. 8, No. 11, Nov. 19, 2013, 6 pages provided.

Pan Sung-Ching et al: "A randomized, double-blind, controlled clinical trial to evaluate the safety and Immunogenicity of an intranasally administered trivalent inactivated influenza vaccine with adjuvant LTh ([alpha]K): A phase I study", Vaccine, vol. 37, No. 14 , available online Mar. 2, 2019, 10 pages provided.

Office Action and Search Report issued in TW109109055, issued Mar. 24, 2021, with English translation.

Doc. Ref. EMEA/CHMP/VWP/244894/2006, European Medicines Agency, Evaluation of Medicines for Human Use, London, Jul. 27, 2006.

Pan, Sung-Ching, et al. "A randomized, double-blind, controlled clinical trial to evaluate the safety and immunogenicity of an intranasally administered trivalent inactivated influenza vaccine with adjuvant LTh (αK): A phase I study." Vaccine 37.14 (2019): 1994-2003. Epub Mar. 2, 2019.

Lin, I-Ping, et al. "*Escherichia coli* heat-labile detoxified enterotoxin modulates dendritic cell function and attenuates allergic airway inflammation." PLOS ONE, vol. 9 Issue 3, published Mar. 17, 2014.

Pan, Sung-Ching, et al. "A double-blind, randomized controlled trial to evaluate the safety and immunogenicity of an Intranasally administered trivalent inactivated influenza vaccine with the adjuvant LTh (αK): A phase II study." Vaccine 38.5 (2020): 1048-1056. Article accepted Nov. 18, 2019.

Office Action issued in corresponding Japanese Application No. 2021-555819, dated Nov. 29, 2022, with machine translation.

Song et al., "Sublingual vaccination with influenza virus protects mice against lethal viral infection", PNAS, Feb. 5, 2008, vol. 105, No. 5, pp. 1644-1649.

International Search Report and Written Opinion, International Patent Application No. PCT/CN2020/079954, Jun. 24, 2020 (10 pages).

* cited by examiner

METHOD OF MODULATING MUCOSAL IMMUNOGENICITY

CROSS-REFERENCE

This application claims the benefit of U.S. Provisional Application No. 62/820,966, filed Mar. 20, 2019, incorporated herein by reference in its entirety.

FIELD OF THE INVENTION

The invention relates to the field of mucosal immunization, and particularly, delivering antigens and immunomodulators to different mucosal sites for immunization.

BACKGROUND OF THE INVENTION

The common practices to enhance immunogenicity of a vaccine involve co-administrating an antigen(s) with an immunomodulator such as an adjuvant. Most antigens of non-living vaccines, such as recombinant, purified or split antigens, are often less immunogenic, and rely on an adjuvant to boost immunogenicity. Adjuvants for vaccination belong to immunomodulators, and their mechanisms involve, but are not limited to, depot formation at the injection site, induction of cytokines and chemokines, activation of resident Langerhans's cell, recruitment of antigen-presenting phagocytic cells (APC), and promotion of homing of antigen-presenting cells to drain lymph nodes, etc. In current adjuvanted vaccines, adjuvants and antigens are pre-mixed and administered simultaneously. Depending on the molecular characteristics of the adjuvants and the nature of the reactive APC, adjuvants modulate the quality and quantity of immunity. Nevertheless, immunomodulators that are administered separately and/or at different points in time are not deemed adjuvants (EMEA/CHMP/VWP/244894/2006). Adjuvants are designed to enhance immune reaction against antigens. Immunomodulators modify the immunity of antigens in more systemic ways.

The mucosal surface is the site most susceptible to pathogen assaults. Mucosal vaccination is an intensively studied vaccination route for effective vaccination, and is recommended in order to provide the first line of defense against infection via mucosal routes. Compared to intramuscular (IM) or subcutaneous (SC) immunization, mucosal immunization offers remarkable public health advantages, which include, but are not limited to, non-invasiveness, cross-reactive IgA to pathogens, low cost, and reduced risk of transmission of blood-borne diseases.

Mucosal epithelium protects the body from environmental assaults, but it is an obstacle to mucosal vaccination. To design an effective mucosal immunomodulator or adjuvant (for vaccine), the abilities to enter or bypass the epithelium barrier, promote uptake of antigens and activate antigen-presenting dendritic cells (DCs) are essential. Langerhans's cells (immature DCs) are common residents in the epithelium. DCs produce dendrite-like pseudopods that extend between stratified squamous epithelium and all the way up to the mucosal surface to sample the environment via surface receptors. This sampling mechanism provides an efficient passage for a mucosal immunomodulator and an antigen to facilitate subsequent uptake by Langerhan's cells. Nowadays, only a handful of mucosal vaccines are available for humans, which is mainly due to the deficiency of safe and effective mucosal adjuvants.

Bacterial components, toxins and toxoids modulate immune responses and are suitable as adjuvants. The

*Escherichia coli* labile toxin (LT) is one of the most studied mucosal adjuvants for its outstanding effectiveness in enhancing immunogenicity.

In general vaccination practice, antigens are premixed and co-administered with adjuvants. The processes of antigen mediated lymphocyte activation involve, briefly, exposing an antigen to immature APC, engulfing the antigen into APC to mature APC, inducing APC to secrete cytokine, recruiting immune cells, homing the matured APC to proximal lymph node (LN), cross-talking between lymphocytes and APC, and activating lymphocytes. The rationale to premix adjuvant with antigen is based on the assumption that antigen alone is insufficient to optimize APC to complete the lymphocyte activation, which also suggests that the simultaneous stimulation of antigen with adjuvant could tune the APC and define its role in subsequent lymphocyte activation.

Influenza vaccination is the most effective method for preventing influenza virus infection and its potentially severe complications. Hemagglutinin (HA) and neuraminidase (NA) proteins are required for such infection and represent the major surface glycoproteins of influenza virion. Because influenza viruses undergo frequent antigenic change on HA and NA (i.e., antigenic drift), persons recommended for vaccination must receive an annual vaccination against the influenza viruses currently in circulation.

Current influenza vaccination enhances anti-viral specific IgG, although lacks amplification to mucosal IgA. The first influenza vaccine was developed in 1938. Since then, intramuscular or subcutaneous administration has been the predominant route of vaccination. However, neither provides mucosal protection. Attenuated seasonal influenza vaccination via nasal spray is now available and provides enhanced mucosal protection, but it is accompanied by some limitations and safety concerns. Low efficacy to aged recipients is another public health concern to current influenza vaccination. To fulfill unmet medical needs, high dose antigens or adjuvant-added vaccines have been approved internationally.

An allergy is a disorder of the immune system and is characterized by the occurrence of allergic reactions to normally harmless environmental substances, which may be present in a wide variety of sources, including, but not limited to, mites, pollens or other plant components, dust, molds or fungi, foods, additives, latex, transfusion reactions, animal or bird dander, insect venoms, radiocontrast medium, medications or chemicals.

House dust mite extracts (HDM) are extracts from house dust mites and are used in allergen immunotherapy (AIT) for an HDM-specific airway allergy. HDM can be administered by either intramuscular (IM) or sublingual (SL) route. However, the immunogenicity of HDM is poor. For an SL route, a daily dosing for 3-5 months per year for 3 or more years is often required to fully alleviate allergic symptoms. Currently, the gold standard for therapeutic efficacy is the titer of allergen-specific IgG4. Many studies have demonstrated that the titers of allergen-specific IgG4 are negatively correlated to airway allergies. Rodents do not have IgG4 and its role is substituted by other IgG subtypes.

In the present invention, it was found that immunomodulators such as LTh(αK), delivered to a different anatomical mucosal site from that to which the antigen is delivered, provided significant enhancement to antigen-specific immune response. The present invention broadens the use of immunomodulators such as LTh(αK) in mucosal immunity as an immunomodulator and its application in the development of mucosal vaccines and therapies for airway allergies.

SUMMARY OF THE INVENTION

The present disclosure relates to the discovery that by administering an antigen and an immunomodulator to different mucosal sites, and the immunogenicity of the antigen can be modulated and a desirable immune response can be elicited. Therefore, the present disclosure provides a novel method for modulating mucosal immune responses, comprising administering an antigen to a mucosal site of a subject in need thereof, and administering an immunomodulator to a different anatomical mucosal site of said subject.

In a preferred embodiment, the antigen is a foreign protein to mammals, such as humans. Particularly, the antigen exhibited unsatisfactory immunogenicity to clinical demand. In a preferred embodiment, the antigen induces mucosal immune response; more preferably, the antigen is involved in pathogenic response. In a preferred embodiment, the antigen consists of viral proteins, pollen, mold, insect proteins (HDM, bee venom, cockroaches, etc.), animal dander, dust, chemicals, plants, etc. In a preferred embodiment, the antigen is biological.

In one embodiment, the immunomodulator can signal through the mucosal epithelium. Preferably, the immunomodulator is a toxin or toxoid, and more preferably, the immunomodulator is a toxin or toxoid of bacterial origin. In a preferred embodiment, the immunomodulator is a detoxified LT, LTh(αK), Toll-Like Receptor (TLR) agonist or antagonist, Vaxfectin, or pattern recognition receptors (PRR) agonist or antagonist. In a further preferred embodiment, the immunomodulator is LTh(αK). LTh(αK) corresponds to LTS61K as disclosed in US 2008102078, which is a detoxified E. coli LT holotoxin with a lysine substitution at the position corresponding to position 61 of SEQ ID NO: 5 as disclosed in US 2008102078. In a further preferred embodiment, the immunomodulator does not induce cytokine IL6 production from cells in contact, including epithelial cells, Langerhan's cells, resident mononuclear cells, and neuronal cells.

In one embodiment, the mucosal site may be any anatomical mucosa. In a preferred embodiment, the mucosal site is sublingual mucosa, intranasal mucosa, respiratory track mucosa, oral mucosa, vaginal mucosa, rectal mucosa, or other anatomical mucosa. In a further preferred embodiment, the antigen is administered to sublingual mucosa. In a further preferred embodiment, the immunomodulator is administered to intranasal mucosa which could extend to the pharynx.

In a preferred embodiment, the immune response involves production of antigen-specific IgG and its subclasses, antigen-specific IgA and its subclasses, antigen-specific IgM and its subclasses, or cell-mediated immunity. More preferably, the immune response provides a therapeutic benefit. In a further preferred embodiment, the immune response involves upregulation of immune components. In another preferred embodiment, the immune response involves downregulation of immune components. In a further preferred embodiment, the immune response involves production of immunoglobulin against the antigen.

In a preferred embodiment, the antigen is administered sequentially or in conjunction with the immunomodulator, but to different mucosal sites. In a further preferred embodiment, the antigen and immunomodulator are administered simultaneously. In a further preferred embodiment, the antigen and immunomodulator are administered separately.

More preferably, the interval between the administration of antigen and the administration of immunomodulator is within 1 minute, 2 minutes, 3 minutes, 5 minutes, 10 minutes, 20 minutes, 30 minutes, 1 hour, 2 hours 3 hours, 4 hours, 5 hours, 6 hours, 12 hours, 1 day, 2 days, 3 days, 4 days or 5 days.

The present invention is described in detail in the following sections. Other characterizations, purposes and advantages of the present invention can be easily found in the detailed descriptions and claims of the invention.

DETAILED DESCRIPTION OF THE INVENTION

Figure 1A:
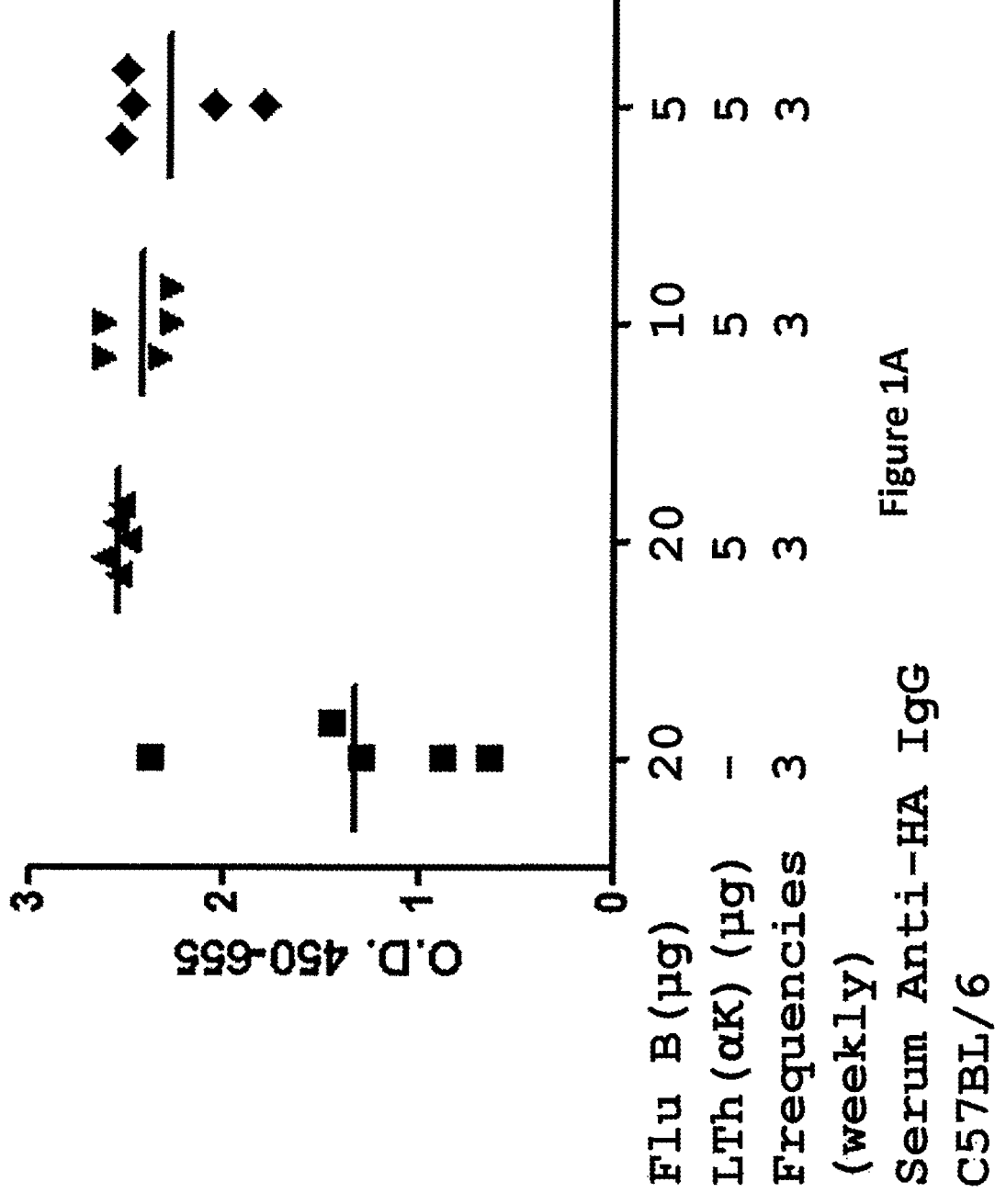
FIGS. 1A-F illustrate antigen-specific immunogenic effect from sublingual vaccinated split influenza B vaccine (B/Brisbane/60/2008-like virus) in conjunction with or without intranasally delivered LTh(αK). Serum (A-D) and nasal wash (E, F) from mice were collected on 14 days post-immunization; and the titers to influenza-B IgG (A, B) and IgA (C-F) were analyzed. The X axis indicates the dosages of HA antigen of Flu B and LTh(αK) in each immunization. Both C57BL/6 (A, C, and E) and Balb/c (B, D, and F) strains were subjected to this study. All animals received three weekly administrations. Serum anti-influenza-B immunoglobulin G and nasal wash anti-influenza-B immunoglobulin A were enhanced following sublingual administration of influenza-B antigens in conjunction with intranasal administration of LTh(αK).
Figure 1B:
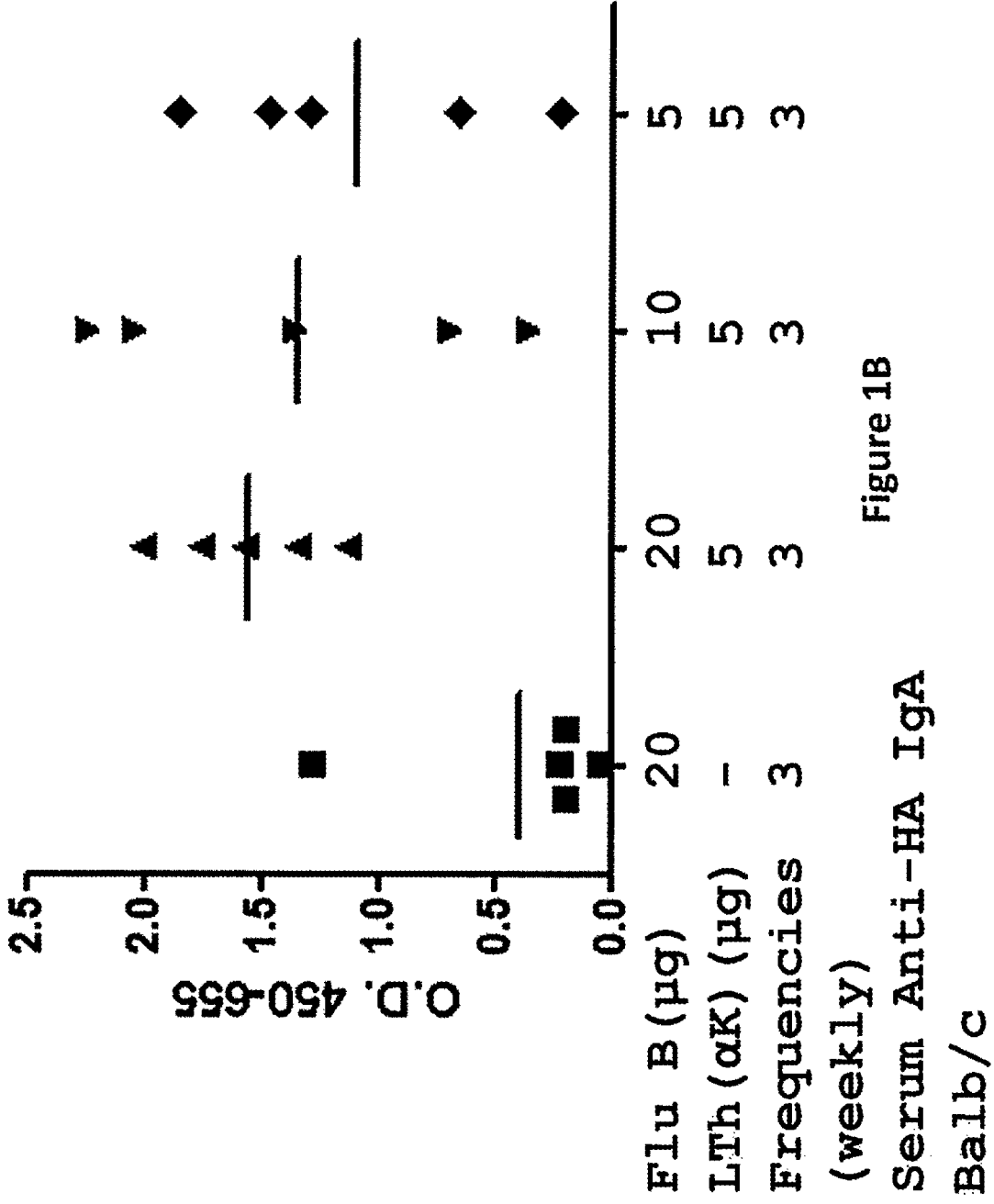
Figure 1C:
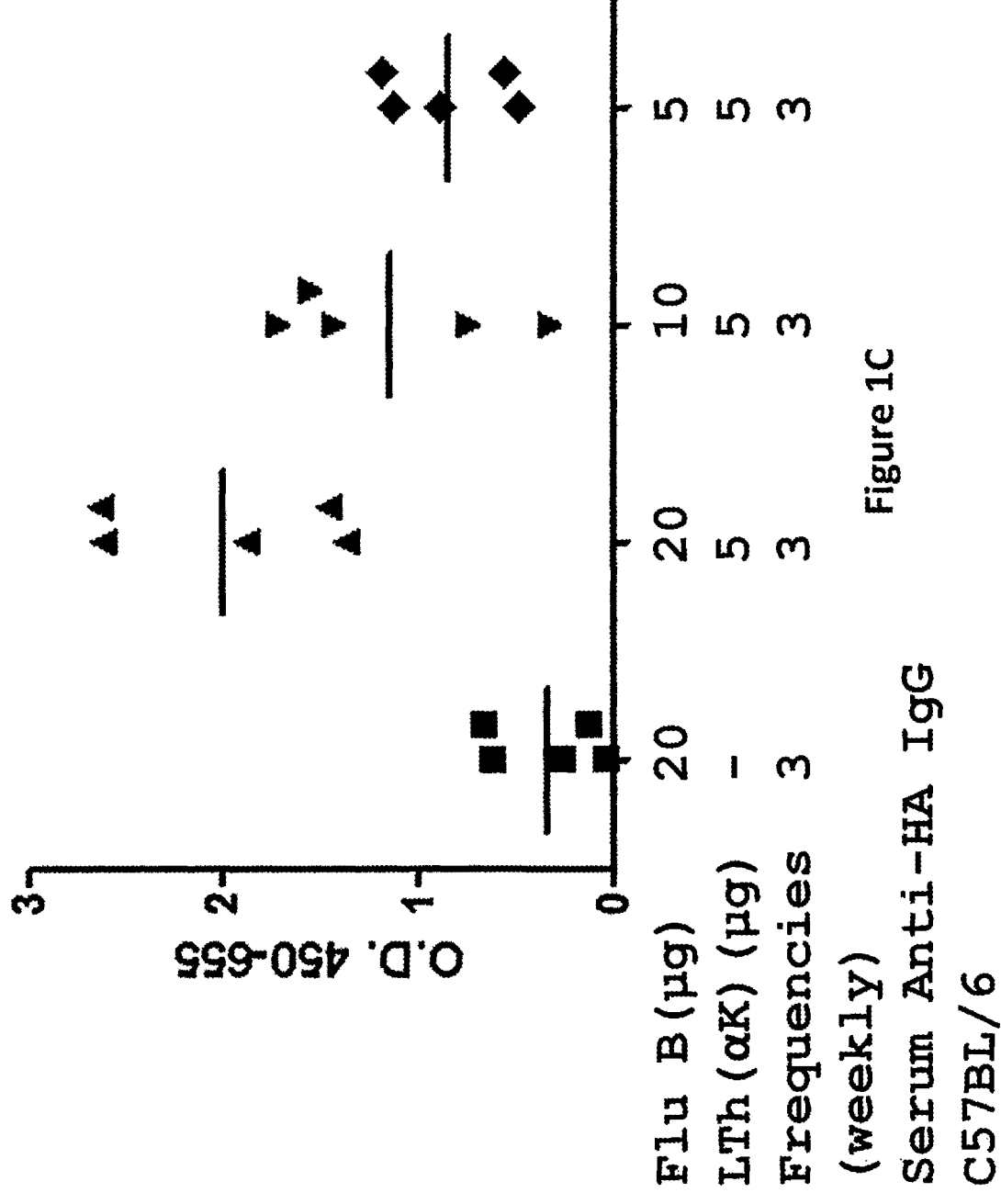
Figure 1D:
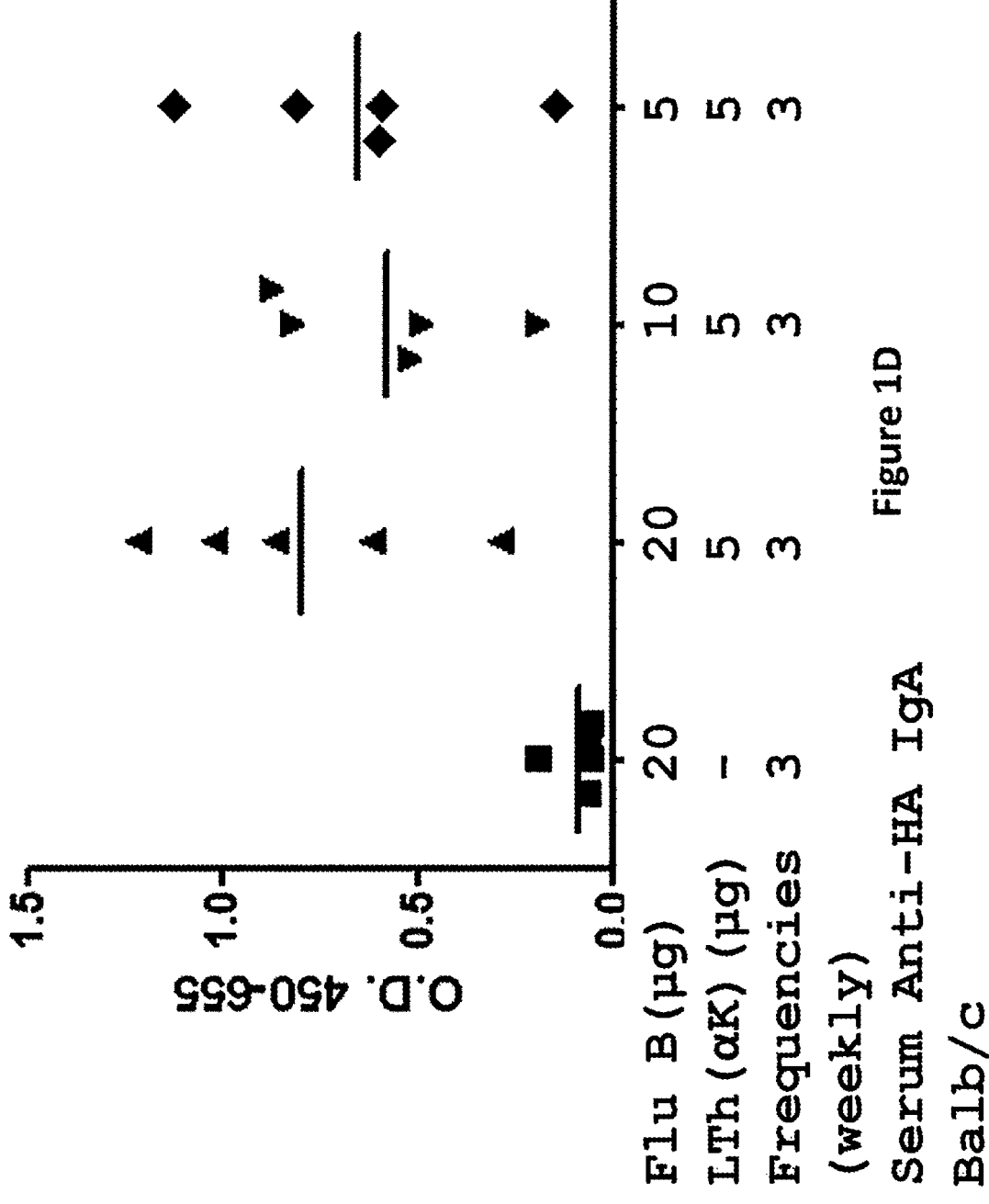
Figure 1E:
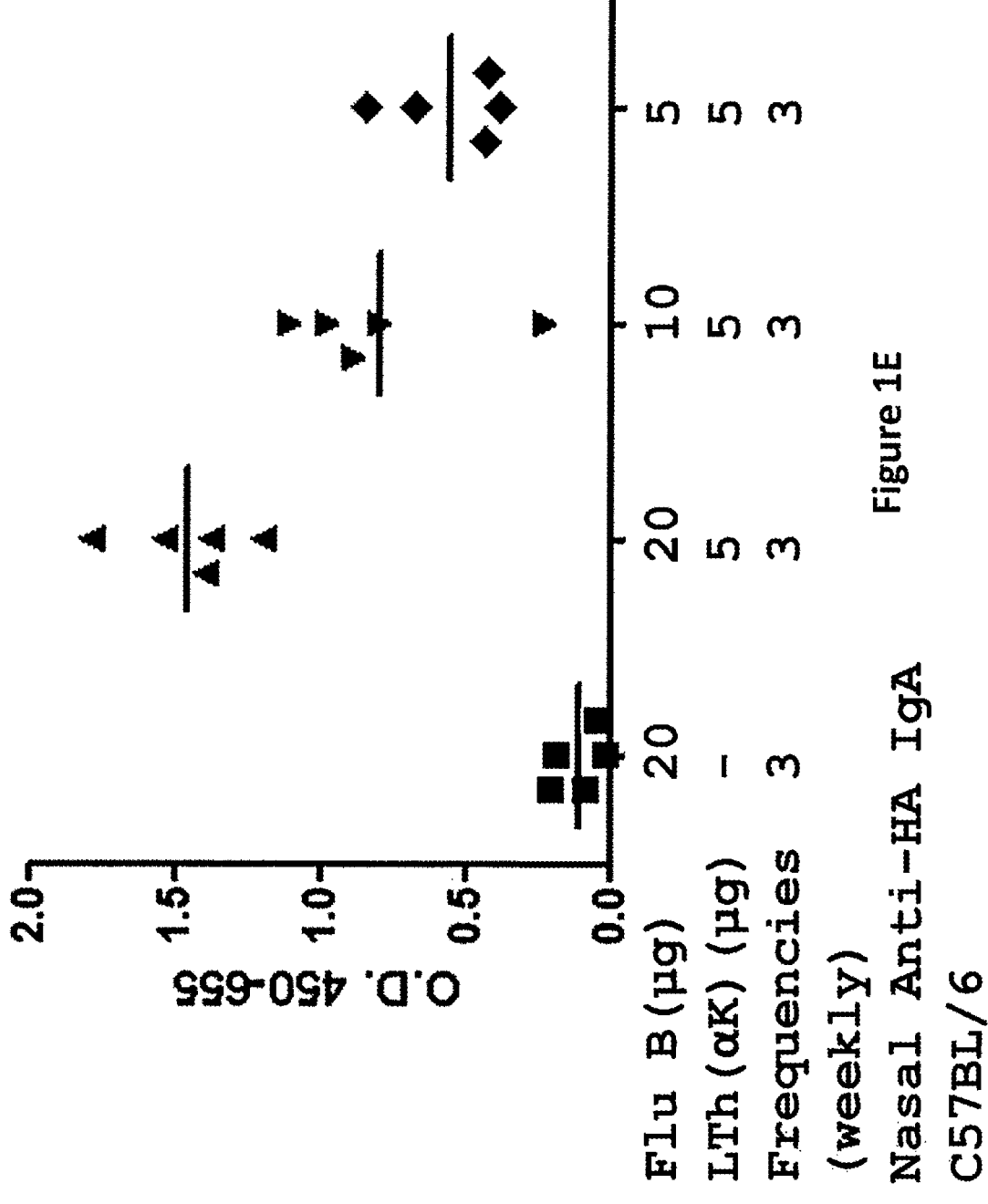
Figure 1F:
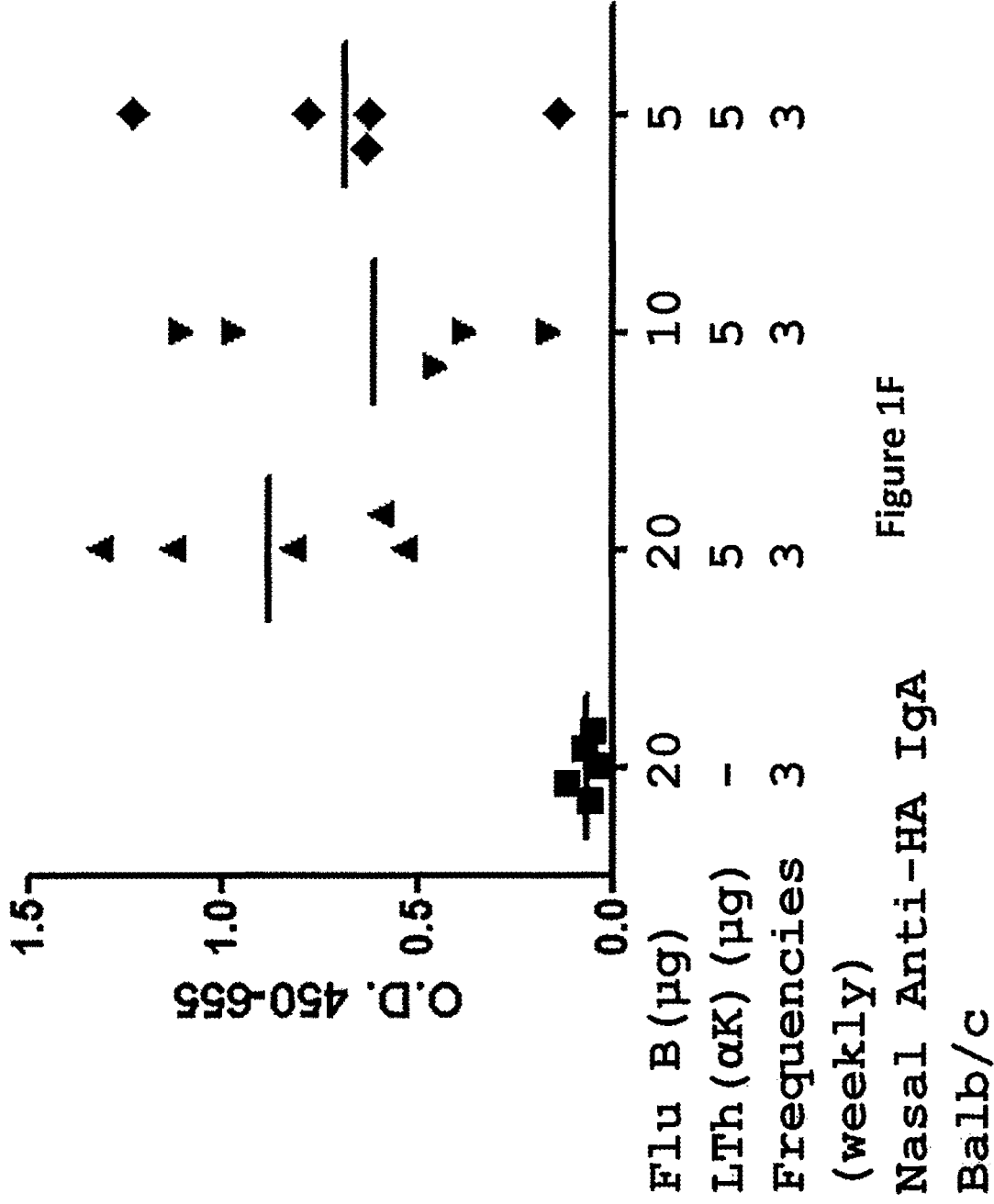
Figure 2A:
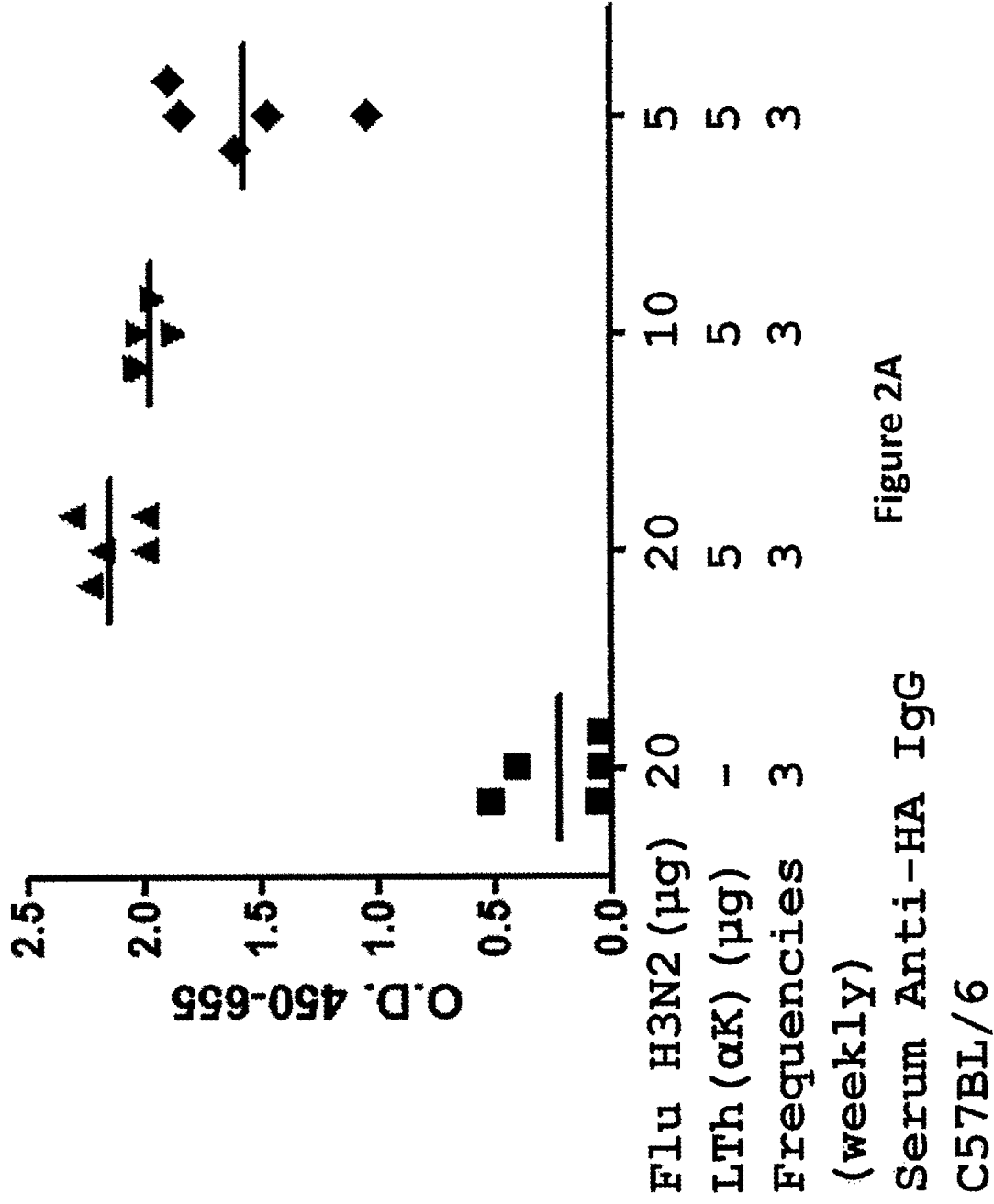
FIGS. 2A-F illustrate antigen-specific immunogenic effects from sublingual vaccinated influenza A (H3N2) vaccine (A/Hong Kong/4801/2014 (H3N2)-like virus) in conjunction with or without intranasally delivered LTh(αK). Serum (A-D) and nasal wash (E, F) were collected on 14 days post-immunization and the titers to influenza-H3N2 IgG (A, B) and IgA (C-F) were analyzed. The X axis indicates the dosages of HA antigen of H3N2 and LTh(αK) in each immunization. Both C57BL/6 (A, C and E) and Balb/c (B, D and F) strains were subjected to this study. All animals received three weekly administrations. Serum anti-Flu (A/H3N2) immunoglobulin G, serum anti-Flu (A/H3N2) immunoglobulin A and nasal wash anti-Flu (A/H3N2) immunoglobulin A were enhanced following sublingual administration of Flu antigens in conjunction with intranasal administration of LTh(αK).
Figure 2B:
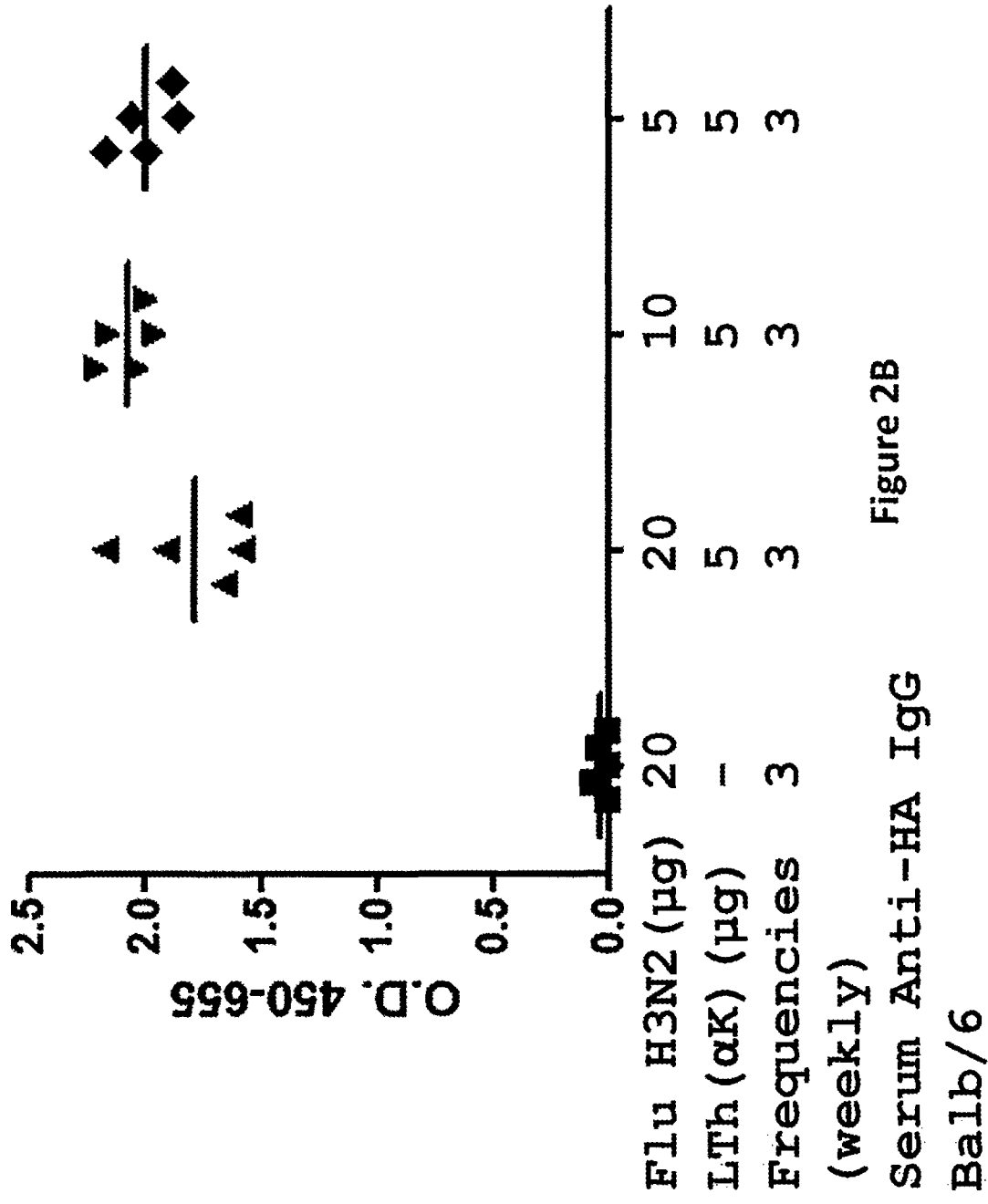
Figure 2C:
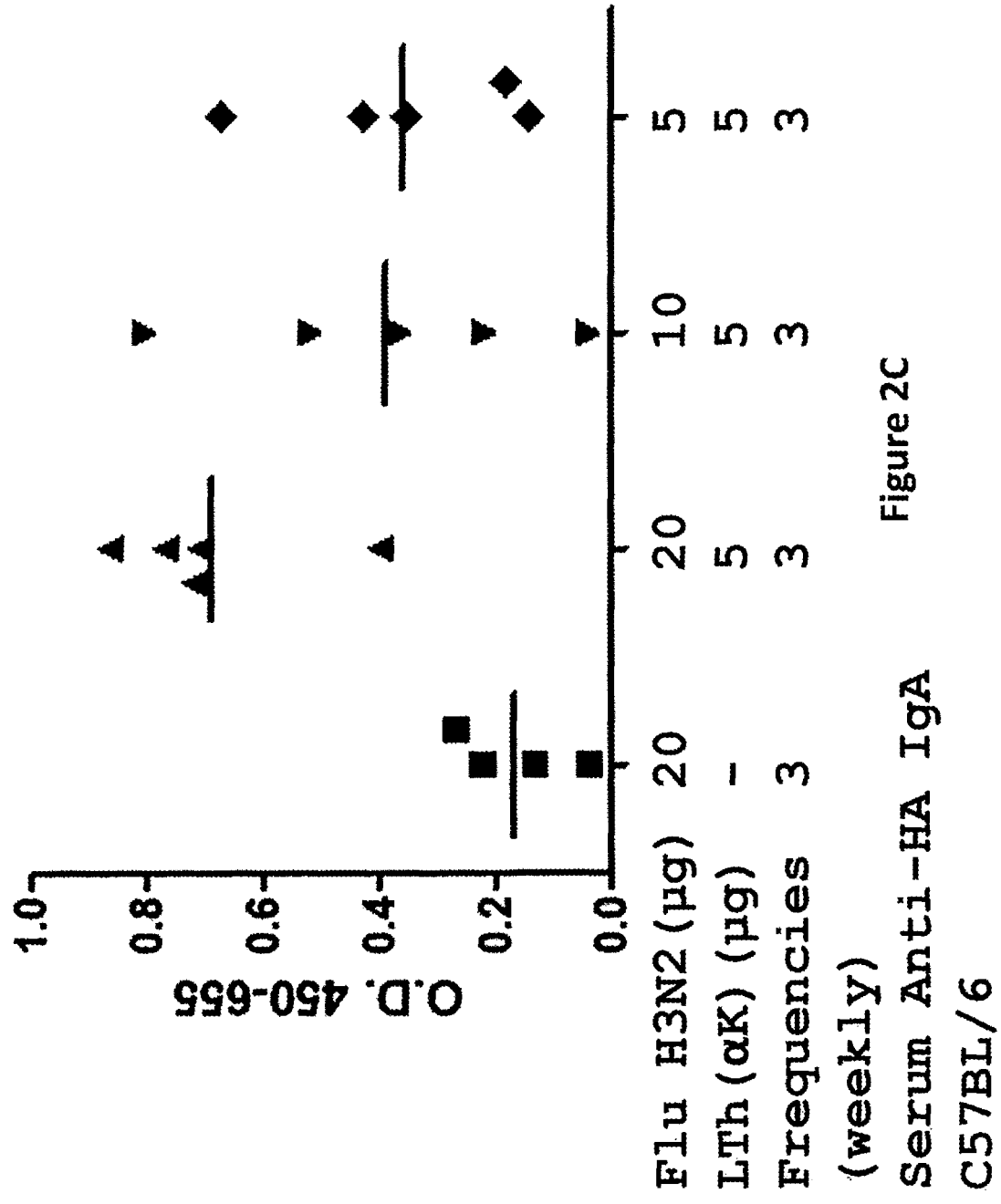
Figure 2D:
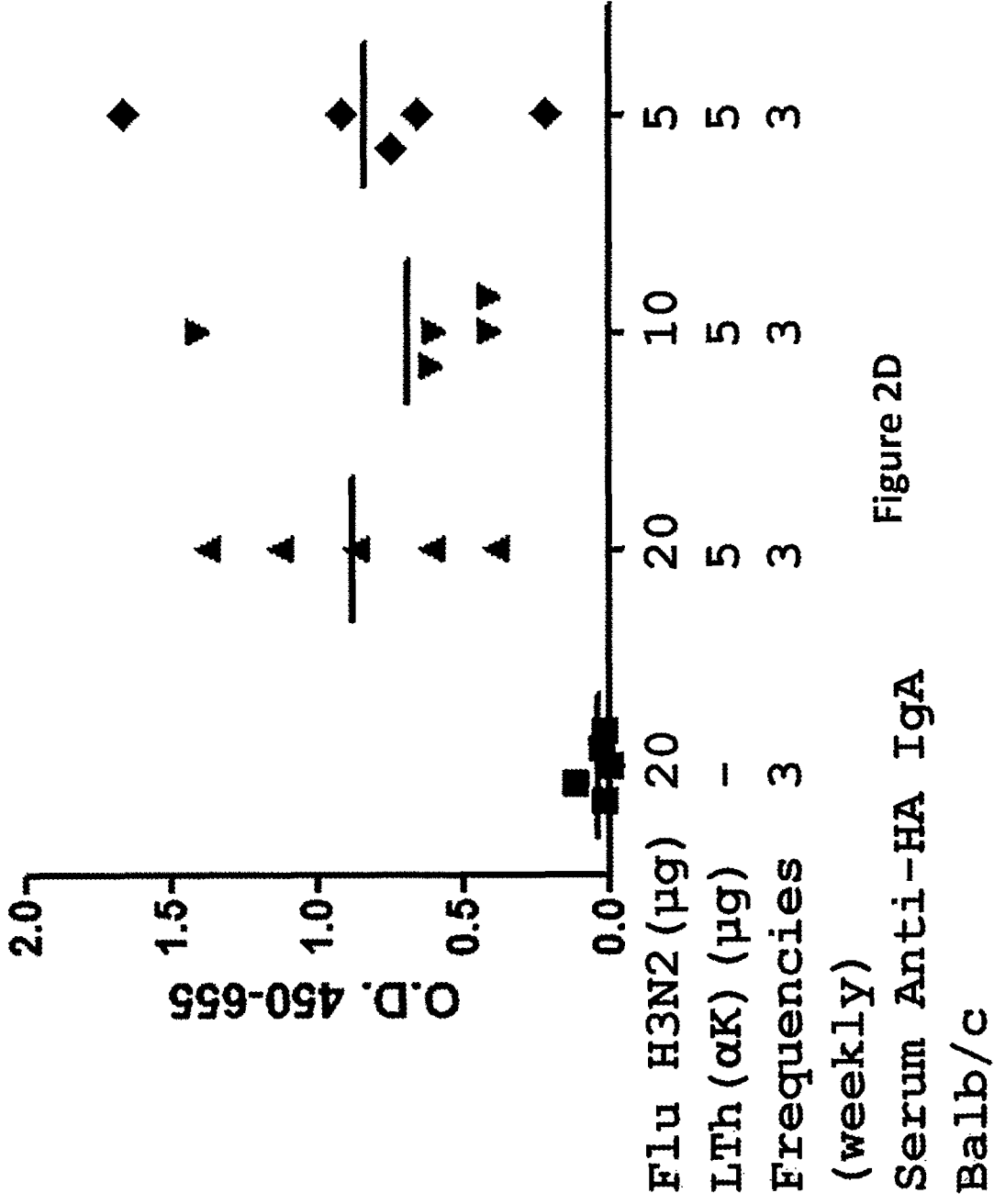
Figure 2E:
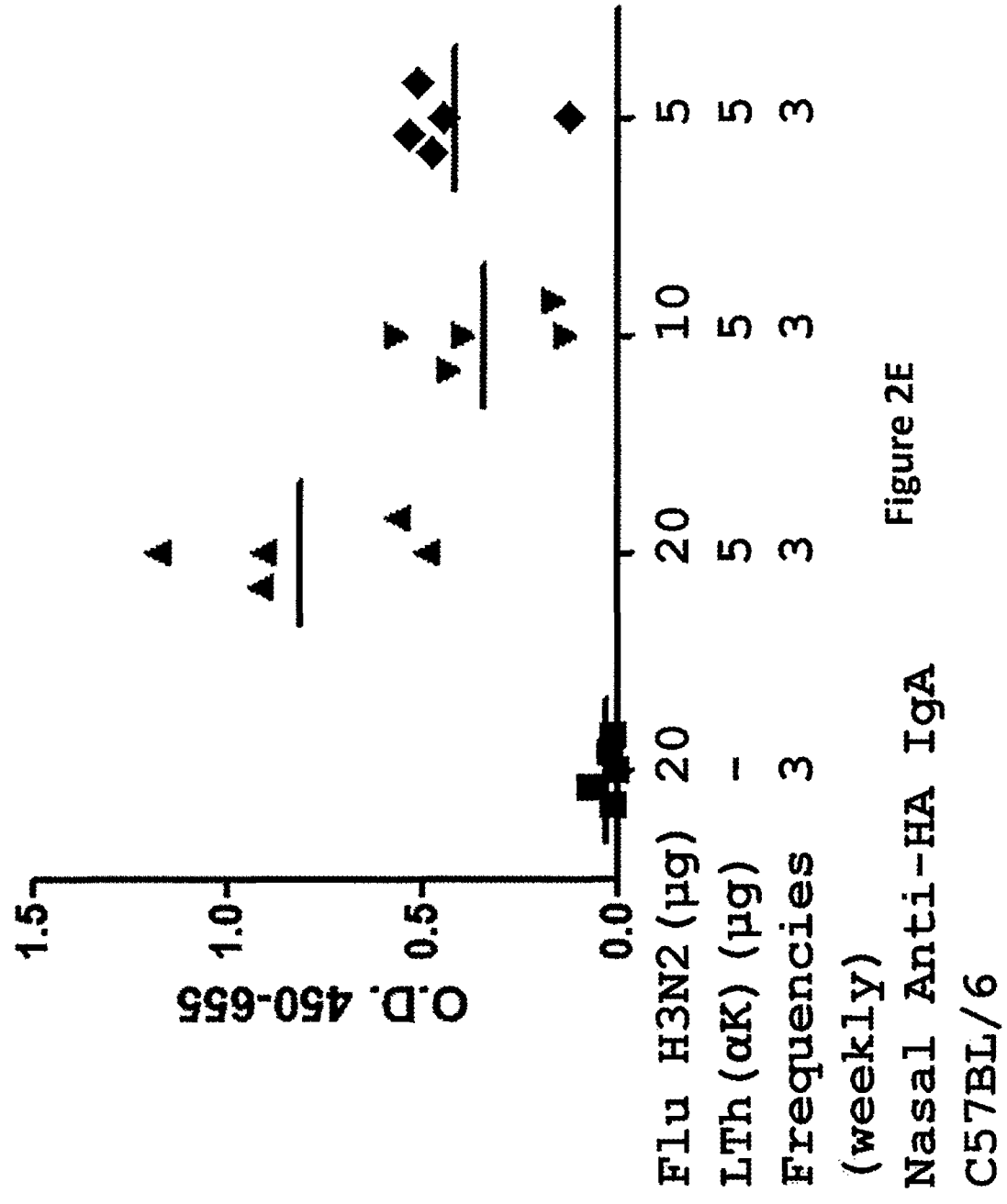
Figure 2F:
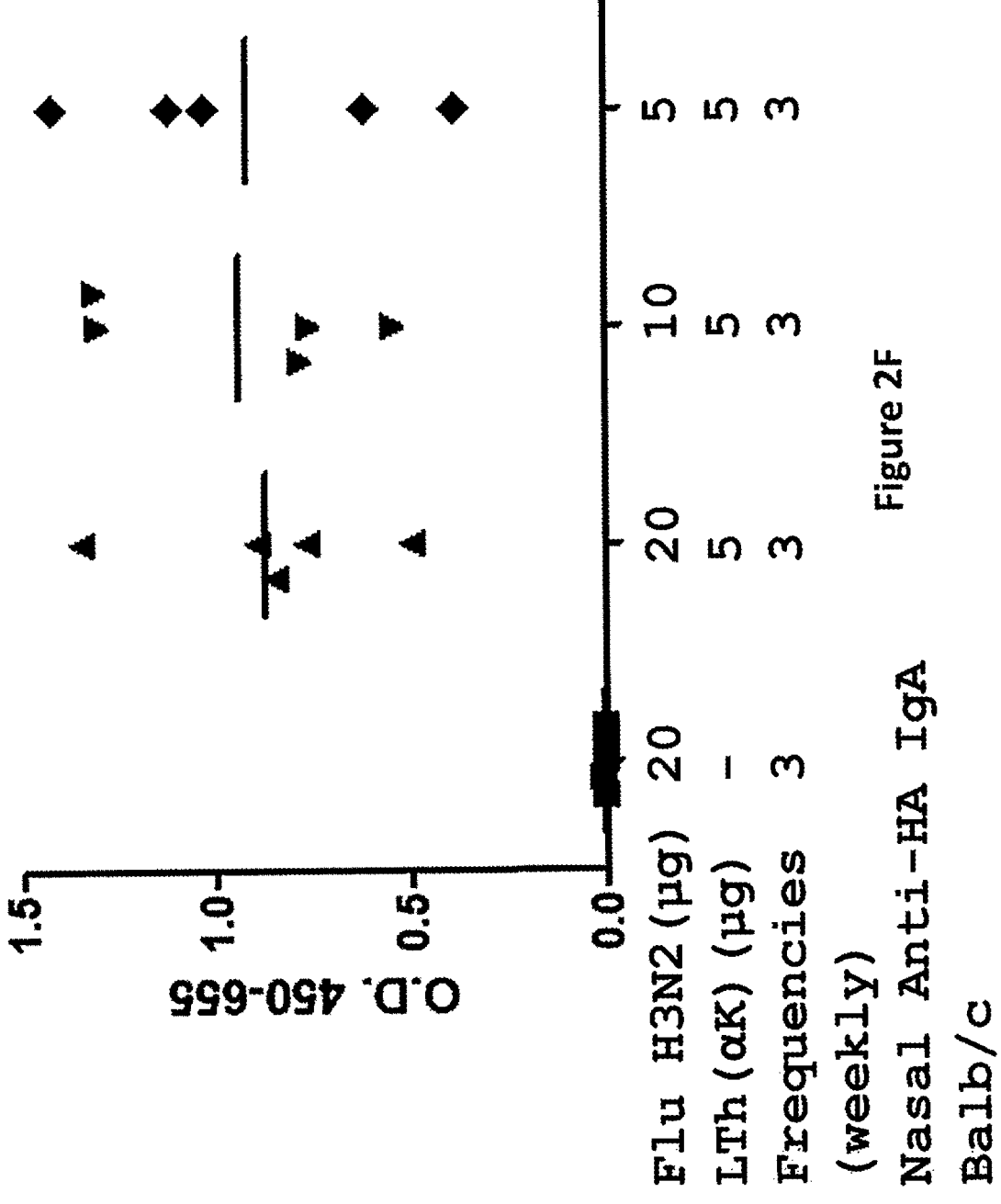

Unless otherwise defined herein, scientific and technical terms used in connection with the present invention shall have the meaning commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The terms "modulating" and "modulation" used herein refer to the regulation of a condition, level, or amount. The regulation may be upregulation or downregulation.

The term "mucosal immune response" used herein refers to immune responses that are induced at the mucosa. For example, mucosal immune response includes, but is not limited to, antigen-specific immunoglobulin G and its subclasses, immunoglobulin A and its subclasses, immunoglobulin M and its subclasses and cell-mediated immunity to immunized antigens.

The term "mucosal site" as used herein refers to any anatomical mucosa covered with mucosal epithelium. For example, the mucosal site may be sublingual mucosa, intranasal mucosa, respiratory track mucosa, oral mucosa, vaginal mucosa, rectal mucosa or other anatomical mucosa.

The term "adjuvant" used herein may be interchangeable with "immunomodulator" and refers to a pharmacological or immunological agent that modifies the immune response to specific-antigens. For example, an adjuvant may be detoxified LT, LTh(αK), Toll-Like Receptor (TLR) agonists or antagonists, Vaxfectin, or pattern recognition receptor (PRR) agonists or antagonists.

The term "immunomodulator" as used herein refers to a pharmacological or immunological agent that modifies the immunity and ultimately changes the outcome of immunogenicity to specific antigens/allergens. For example, an immunomodulator may be detoxified LT or Toll-Like Receptor (TLR) agonists.

The term "subject" as used herein denotes animals, especially mammals. In one preferred embodiment, the term "subject" denotes humans.

Unless otherwise required by context, singular terms shall include the plural and plural terms shall include the singular.

The inventors of the invention surprisingly found that, contrary to the traditional way of mixing adjuvant with antigen for enhancing a specific immune response, separately administering the immunomodulator and antigen to different mucosal sites can significantly enhance desirable mucosal immune response. In addition, it is not required to administer the immunomodulator and antigen at the same time. The antigen and immunomodulator may be administered sequentially with interval within minutes to days as described herein. The present invention provides a novel role of immunomodulator in mucosal immunity and may facilitate the development of novel mucosal vaccine administration beyond traditional means.

Having now generally described the invention, the same may be more readily understood through reference to the following examples, which provide exemplary protocol for performing the method of the present invention in modulating mucosal immune response. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Mice used in the subsequent examples were female, purchased from BioLASCO Taiwan Co., Ltd. and housed under specific-pathogen-free (SPF) conditions. Studies were initiated at 8 weeks of age. For sublingual administration, mice were lightly anesthetized by inhaling isoflurane, and then sublingually administered with a single 12 μL treatment in a secured lying position for 25 seconds. For intranasal administration, mice received a single volume of 2.5 μL of treatment to each nostril. Both Balb/c and C57BL/6 mice were used in Examples 1 to 4.

Example 1: Evaluation of the Immunogenic Effects of the Mucosal Immunomodulator LTh(αK) for the Influenza B Vaccine In FIG. 1, mice received sublingually administered Flu B and some received intranasally administered LTh(αK) as co-treatment through intranasal route (FIG. 1). In the first group, each mouse received 20 μg of Flu B sublingually. In the 2, 3, and 4 groups, mice received 20, 10, and 5 μg of Flu B, respectively, through sublingual route in conjunction with 5 μg of LTh(αK) intranasally. In all groups, treatments were given one week apart for a total of three treatments.

Blood and nasal wash from the studied mice were collected at 14 days post-treatment. The anti-Flu B IgG and IgA were assayed by ELISA. The results are shown in FIG. 1.

LTh(αK) administered through intranasal route enhanced the humoral and mucosal immunity against sublingually administered Flu B vaccine (FIGS. 1A-D). Flu B was a poor mucosal immunogen as it induced low titers of serum Flu B-specific IgG and minimal IgA following sublingual administration (group 1, FIGS. 1A-D). Additional LTh(αK) via intranasal route enhanced the serum Flu B-specific IgG and IgA titers. The enhancement of Flu B-specific IgG and IgA was revealed on two strains of mice (FIGS. 1A-D). Balb/c and C57BL/6 mice have been known to demonstrate biased immunological responses toward Th2 and Th1, respectively. The above results of the immunologically distinct mice suggest that animals with different immunogenetic backgrounds may be applicable in the present invention.

Mucosal-specific anti-Flu B IgA was revealed only in groups co-treated with LTh(αK) (FIGS. 1C-F). IgA is the hallmark of mucosal immunity and the frontline to defend against most infections. When Flu B was administered alone by sublingual route, Flu B-specific IgAs were not enhanced (groups 1, FIGS. 1C-E).

In conclusion, the administration of LTh(αK) by intranasal route significantly enhanced Flu B-specific IgG and IgA titers induced by SL administration. The same results were revealed on both Balb/c and C57BL/6 mice.

Example 2: Evaluation of the Immunogenic Effects of the Mucosal Immunomodulator LTh(αK) for the Influenza A Vaccine In FIG. 2, mice received sublingually administered Flu A/Hong Kong/4801/2014 (H3N2)-like virus vaccine (Flu A) and some received co-treatment of intranasally administered LTh(αK) (FIG. 2). In the first group, each mouse received 20 μg of Flu A sublingually. In the 2, 3, and 4 groups, mice received 20, 10, and 5 μg of Flu A, respectively, through sublingual route in conjunction with 5 μg of LTh(αK) intranasally. In all groups, treatments were given one week, separately, for a total of three treatments.

Blood and nasal wash from the studied animals were collected at 14 days post-immunization for all mice. Anti-Flu A IgG and IgA were assayed by ELISA. The results are shown in FIG. 2.

LTh(αK) administered through intranasal route enhanced the humoral and mucosal immunity against sublingually administered Flu A vaccine (FIGS. 2A-D). Flu A is a poor mucosal immunogen as it induced low titers of serum Flu A-specific IgG and minimal IgA following sublingual administration (group 1, FIGS. 2A-D). Additional LTh(αK) via intranasal route enhanced the serum Flu A-specific IgG and IgA titers. The enhancement of Flu A-specific IgG and IgA was revealed on both strains of mice (FIGS. 2A-D). Balb/c and C57BL/6 mice have been known to demonstrate biased immunological responses toward Th2 and Th1, respectively. The above results of the immunologically distinct mice suggest that animals with different immuno-genetic backgrounds may be applicable in the present invention.

Mucosal-specific anti-Flu A IgA was revealed only in groups co-treated with LTh(αK) (FIGS. 2C-F). IgA is the hallmark of mucosal immunity and the frontline to defend against most infections. When Flu A was administered alone by sublingual route, Flu A-specific IgAs were not enhanced (groups 1, FIGS. 2C-E).

In conclusion, the administration of LTh(αK) by intranasal route significantly enhanced Flu A-specific IgG and IgA titers induced by SL administration. The same results were revealed on both Balb/c and C57BL/6 mice.

Example 3: Evaluation of the Immunogenic Effects of the Mucosal Immunomodulator LTh(αK) for the House Dust Mite Extract Mice were pre-treated with HDM extract, which was purchased from Stallergenes Greer (XPB70D3A2.5), via sublingual route with or without immunomodulator (LTh (αK)) co-treatment by intranasal route. To simulate the allergic reactions, following pretreatment, mice s were sensitized once intratracheally and challenged five times intranasally with HDM extract. Blood samples and bronchoalveolar lavage fluid (BALF) were collected on 4 days post final challenge and HDM-specific IgG and IgA were assayed by ELISA.

Figure 3A:
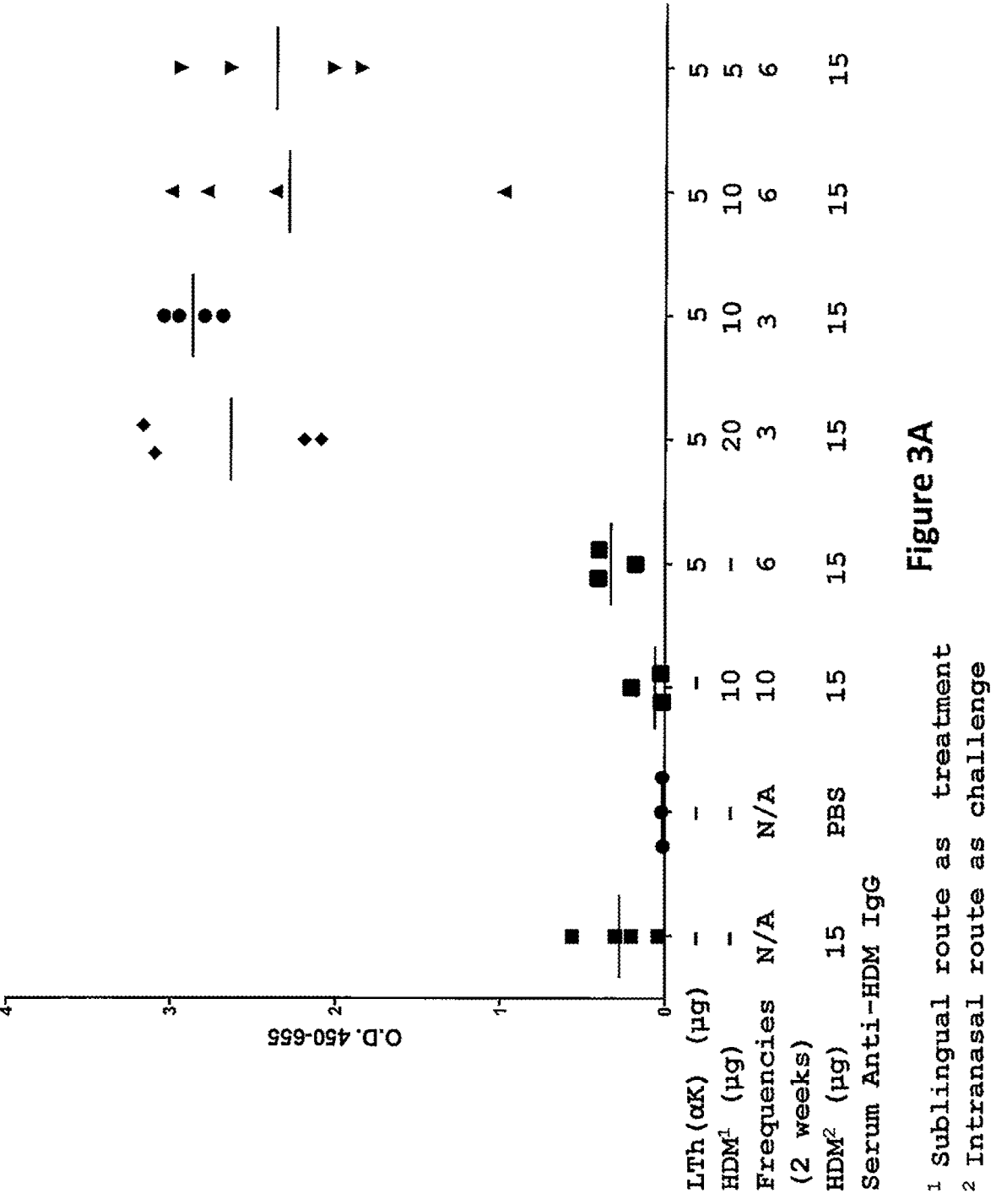
FIGS. 3A and 3B illustrate antigen-specific immunogenic effects from sublingual administered allergens (HDM, purchased from Greer Laboratories, catalog number: XPB70D3A2.5), in conjunction with or without intranasally administered LTh(αK) following additional HDM challenges. Serum (A) and nasal wash (B) were collected; and IgG (A) and IgA (B) titers to HDM were analyzed. The treatment lasted two weeks. The X axis indicates the dosages of HDM and LTh(αK), and the total number of treatments. Balb/c mice were subjected to this study.
Figure 3B:
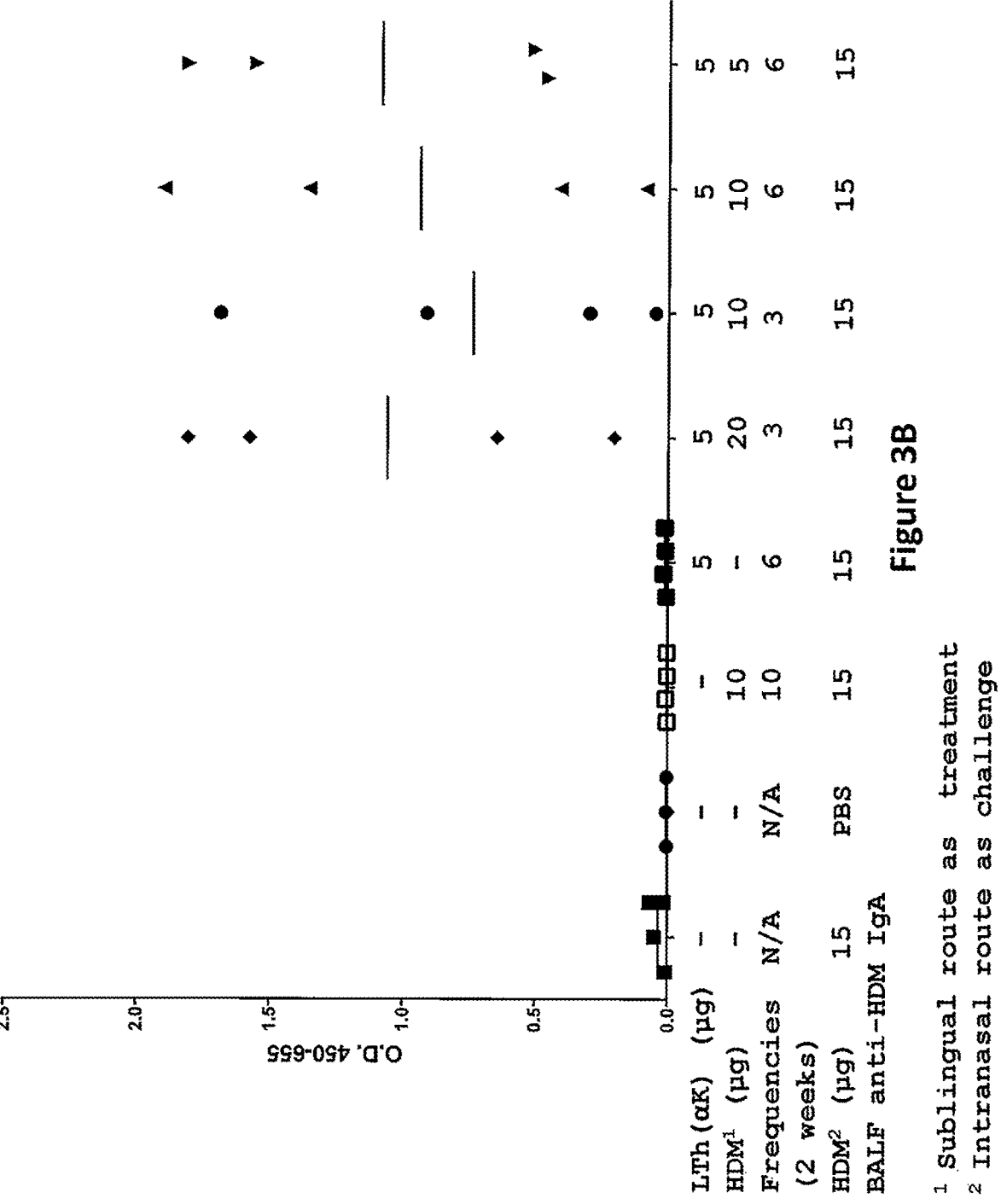

The results showed that intranasal administration of LTh (αK) enhanced humoral and mucosal immunity to sublingually and intranasally administered HDM extract (FIGS. 3A and 3B). Group 1 was the positive control group. Mice of this group received intranasal HDM extract for sensitization and challenges without prior HDM extract treatment. Group 2 was the healthy control group. Mice in this group received neither treatment nor challenge. Group 3 was the allergen immunotherapy (AIT) group. Mice of this group received 10 doses of sublingual HDM extract treatment in two weeks prior to intranasal HDM extract sensitization and challenge. Group 4 was the LTh(αK) control group. Mice of this group received 6 doses of LTh(αK) treatment via intranasal route in two weeks, followed by intranasal HDM extract sensitization and challenges. Groups 5 to 8 were co-treatment groups. Mice of these groups received co-treatment of HDM extract and LTh(αK) at various quantities via sublingual and intranasal routes, respectively, followed by intranasal HDM extract sensitization and challenges. The results demonstrate significantly elevated anti-HDM IgG in serum and IgA in BALF in groups with intranasal co-treatment of LTh(αK).

Figure 4A:
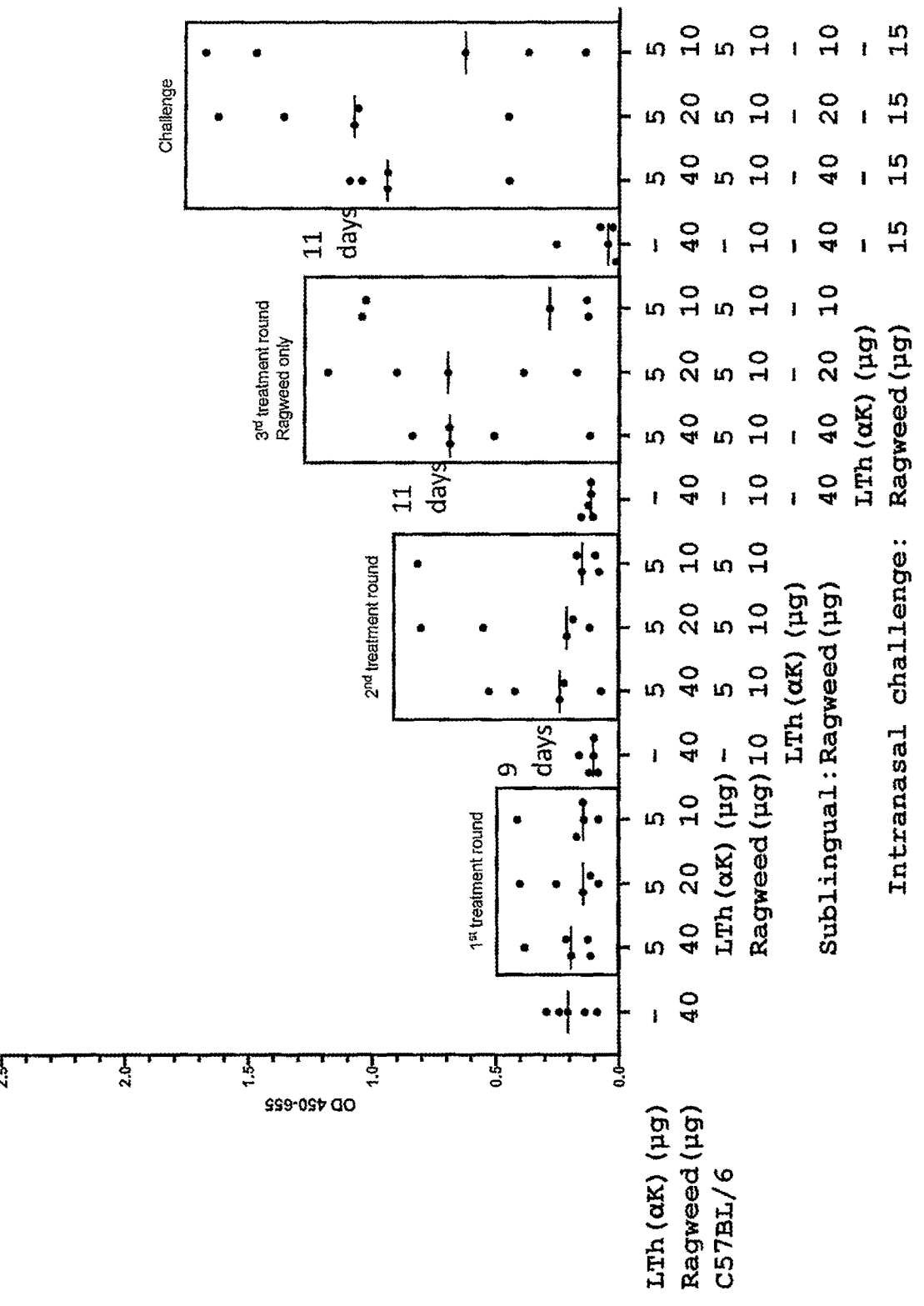
FIGS. 4A and 4B illustrate antigen-specific immunogenic effects from two rounds of sublingually delivered allergens (ragweed, purchased from Greer Laboratories, catalog number: XP56D3A25), in conjunction with or without intranasally delivered LTh(αK) treatments, and an additional ragweed-only treatment followed by ragweed challenges via intranasal route. Mouse sera were collected at the end of study and ragweed-specific IgG titers were analyzed. Each treatment round lasted two weeks. The X axis indicates the dosages of ragweed and LTh(αK), and the total number of treatments. In each treatment, ragweed or LTh((K) was administered 6 times. In the challenge phase, ragweed was administered 5 times daily. C57BL/6 (A) and Balb/c (B) mice were subjected to this study.
Figure 4B:
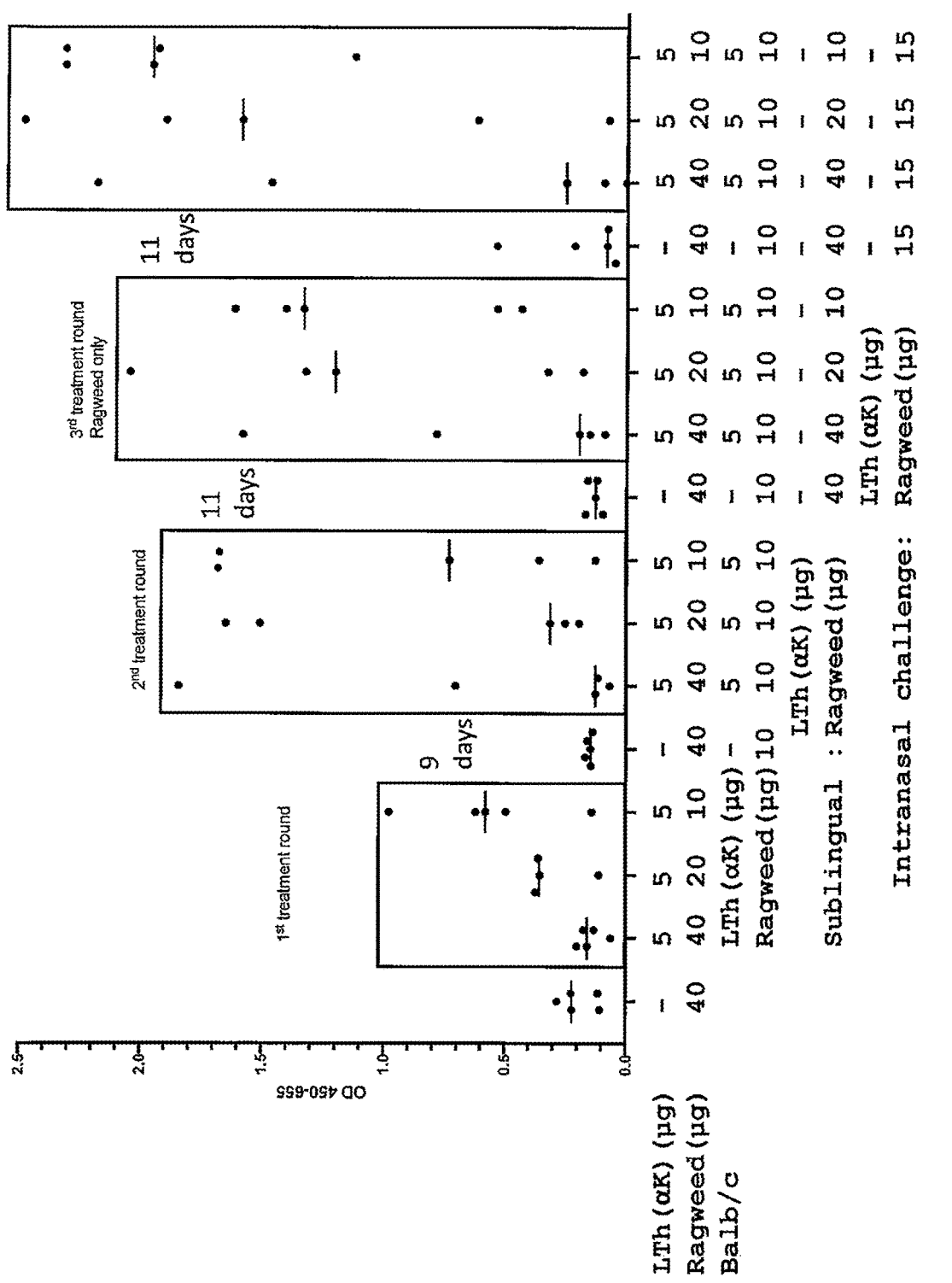

Example 4: Evaluation of the Immunogenic Effect of the Mucosal Immunomodulator LTh(αK) for the Ragweed Pollen Extract To demonstrate the effectiveness of LTh(αK) in enhancing anti-pollen IgG, four groups of mice were given three sublingual rounds of ragweed pollen extract (ragweed) with or without co-treatment of intranasal LTh(αK), followed by airway challenges by ragweed (FIG. 4). In the first round of treatment, group 1 received 6 sublingual doses of ragweed at 40 μg each without LTh(αK). Groups 2, 3, and 4 received 40, 20, and 10 μg of sublingual ragweed, respectively, in conjunction with 5 μg of LTh(αK) intranasally. In the second round, which started 9 days after the end of first treatment round, the mice of group 1 had an additional 6 doses of intranasal ragweed at 10 μg each over two weeks. Groups 2, 3, and 4 received sublingual dosing of 10 μg ragweed and co-treatment of 5 μg LTh(αK) intranasally. The third round was initiated on 11 days after the $2^{nd}$ treatment. This is an AIT-like treatment, and the animals were dosed 6 times sublingually only with ragweed. As shown in FIGS. 4A and 4B, groups 1 and 2 received 40 μg and groups 3 and 4 had 20 and 10 μg of ragweed, respectively. The final challenge started on the $11^{th}$ day after the third treatment round. In the challenge, the animals received five repeated intranasal ragweed at 15 μg each followed by specimen collection. Balb/c and C57BL6 mice have been known to demonstrate biased immunological responses toward Th2 and Th1, respectively. The above results of the immunologically distinct mice suggest that animals with different immuno-genetic backgrounds may be applicable in the present invention. Based on such results, it is concluded that the amounts of anti-ragweed IgG in both Balb/c and C57BL/6 mice were elevated by co-treatment of LTh(αK). In addition, IgG enhancement to allergen lasted weeks after treatment of LTh(αK).

Ragweed in this study was purchased from Stallergenes Greer (XPB56D3A25). Blood samples were collected from pre-immune, and from a week post-treatment and final challenge. Ragweed-specific IgGs were assayed by ELISA.

What is claimed is:

1. A method of modulating a mucosal immune response, comprising:
   administering an antigen to a sublingual mucosa or an oral mucosa of a subject in need thereof; and
   administering an immunomodulator to an intranasal mucosa of said subject,
   wherein the antigen is an immunogen, and the immunomodulator is detoxified *Escherichia coli* heat-labile toxin (LTh (αK)).

2. The method of claim 1, wherein the antigen is a vaccine.

3. The method of claim 1, wherein the antigen is an allergen.

4. The method of claim 1, wherein the antigen is a biological immunogen.

5. The method of claim 1, wherein the immunomodulator does not induce IL6 production from cells with which the immunomodulator comes into contact.

6. The method of claim 1, wherein the immune response comprises production of antigen-specific IgG and one or more subclasses thereof.

7. The method of claim 1, wherein the immune response comprises production of antigen-specific Ig M and one or more subclasses thereof.

8. The method of claim 1, wherein the immune response comprises production of antigen-specific IgA and one or more subclasses thereof.

9. The method of claim 1, wherein the immune response comprises production of antigen-specific cell-mediated immunity.

10. The method of claim 1, wherein the immune response is therapeutically effective.

11. The method of claim 1, wherein the immune response involves upregulation of immune components.

12. The method of claim 1, wherein the immune response involves downregulation of immune components.

13. The method of claim 1, wherein the antigen is administered to sublingual mucosa and the immunomodulator is administered to intranasal mucosa.

14. The method of claim 2, wherein the vaccine is seasonal influenza vaccine.

15. The method of claim 14, wherein the seasonal influenza vaccine is an influenza A virus-like vaccine or influenza B virus-like vaccine.

16. The method of claim 3, wherein the allergen is dust mite extracts or pollen extracts.

17. The method of claim 16, wherein the pollen is ragweed pollen.

18. The method of claim 1, wherein the antigen and the immunomodulator are sequentially administered.

\* \* \* \* \*